US012714354B2

(12) United States Patent
Chen et al.

(10) Patent No.: US 12,714,354 B2
(45) Date of Patent: Aug. 25, 2026

(54) APPARATUS AND METHOD FOR PACE PULSE DETECTION

(71) Applicant: Drägerwerk AG & Co. KGaA, Lübeck (DE)

(72) Inventors: Yu Chen, Andover, MA (US); Kristen M. Bean, Newburyport, MA (US)

(73) Assignee: Drägerwerk AG & Co. KGaA, Lübeck (DE)

( * ) Notice: Subject to any disclaimer, the term of this patent is extended or adjusted under 35 U.S.C. 154(b) by 608 days.

(21) Appl. No.: 17/921,492

(22) PCT Filed: Apr. 30, 2021

(86) PCT No.: PCT/EP2021/061408
§ 371 (c)(1),
(2) Date: Oct. 26, 2022

(87) PCT Pub. No.: WO2021/219851
PCT Pub. Date: Nov. 4, 2021

(65) Prior Publication Data

US 2023/0190169 A1 Jun. 22, 2023

Related U.S. Application Data

(60) Provisional application No. 63/018,861, filed on May 1, 2020.

(51) Int. Cl.
*A61B 5/349* (2021.01)
*A61B 5/00* (2006.01)

(52) U.S. Cl.
CPC ............ *A61B 5/349* (2021.01); *A61B 5/7217* (2013.01); *A61B 5/7221* (2013.01)

(58) Field of Classification Search
None
See application file for complete search history.

(56) References Cited

U.S. PATENT DOCUMENTS 5,891,048 A 4/1999 Nigam et al.
10,004,414 B2 * 6/2018 Brodnick ............... A61B 5/349
(Continued)

FOREIGN PATENT DOCUMENTS

CN 108744284 A 11/2018
EP 2510974 B1 12/2013
WO 2013162613 A1 10/2013

OTHER PUBLICATIONS

European Patent Office, The International Search Report and The Written Opinion of the International Searching Authority, Jul. 7, 2021, for International Application No. PCT/EP2021/061408.

*Primary Examiner* — Michael W Kahelin
(74) *Attorney, Agent, or Firm* — Nolte Lackenbach Siegel

(57) ABSTRACT

An apparatus and method for detecting a pace pulse signal are described. The apparatus and the method include receiving a plurality of sample signals from one ECG lead, measuring a first-level noise of the plurality of sample signals during a first time interval, measuring a second-level noise of the plurality of sample during a second time interval, where the second time interval is different from the first time interval, generating one or more dynamic thresholds based on at least one of the measured first-level noise and the second-level noise, and detecting, based on the one or more dynamic thresholds, at least one of a start point, a peak point and an endpoint of the pace pulse signal from the plurality of sample signals.

12 Claims, 7 Drawing Sheets

(56) References Cited

U.S. PATENT DOCUMENTS

| | | | | |
|---|---|---|---|---|
| 2015/0148696 | A1* | 5/2015 | Lall | A61B 5/349<br>600/510 |
| 2015/0305642 | A1 | 10/2015 | Reinke et al. | |
| 2017/0224242 | A1* | 8/2017 | Brodnick | A61N 1/371 |
| 2018/0078210 | A1* | 3/2018 | Snow | G16H 40/63 |

* cited by examiner

APPARATUS AND METHOD FOR PACE PULSE DETECTION

CROSS-REFERENCE TO RELATED APPLICATIONS

This is a nationalization under 35 U.S.C. § 371 of International Application PCT/EP2021/061408, filed Apr. 30, 2021, under the Patent Cooperation Treaty, which International Application claimed priority to U.S. Application Ser. No. 63/018,861, filed May 1, 2020. The priority and/or earlier effective filing dates of PCT/EP2021/061408 and U.S. Application Ser. No. 63/018,861 are hereby claimed for all purposes.

TECHNICAL FIELD

The present disclosure relates generally to the field of pace pulse detection. More particularly, the present disclosure relates to the detection of pace pulse from electronic pacemakers.

BACKGROUND

Pacemakers are electronic medical devices used by patients with abnormal heart rates or arrhythmias. Pacemakers initiate cardiac cycles by providing stimulus (e.g., pulse) to heart muscle in a well-controlled manner such that the heart can maintain a normal level of function. It is important to detect pace pulses generated by pacemakers while measuring electrocardiogram (ECG) signals of the patient, such that care providers can rely on the measured ECG signals to accurately determine cardiac conditions of the patient. On the other side, misdetection of a pacer pulse or misinterpretation as a QRS complex (e.g., combination of the Q, R, and S graphical deflections which are seen on a typical electrocardiogram) may have significant adverse effects on the diagnosis of the patient.

Detection of pace pulses from pacemakers using surface ECG leads is challenging, because pace pulse signals have a small amplitude and/or narrow width, as well as complicated morphology. In clinical settings, an incorrectly configured pacemaker may also cause repeated false alarms and desensitization to monitoring devices. In addition, it is difficult for monitoring devices to detect pace pulses from different pacemakers, which have become increasingly sophisticated, with high sensitivity and reliability.

One example is a leadless pacemaker that is implanted directly into the right ventricle of the heart. Another example is His bundle pacing, where the pacemaker lead is placed at the atrial portion against the septum and activates ventricles via the native His-Purkinje system. Both leadless pacing and His bundle pacing approaches provide low stimulation energy and generate pace pulses with small amplitude and narrow width, both of which are near or below the detection thresholds of monitoring devices.

Accordingly, there exists a need for improved detection of pace pulses from pacemakers with reduced false-negative rate and/or capability of rejecting false pulse signals with reduced false-positive rate. Further, there exists a need for improved detection/recognition of small pace pulses and improved rejection of large pace pulses to increase sensitivity, specificity, and accuracy of measurements using monitoring devices.

BRIEF DESCRIPTION OF THE DRAWINGS

In the drawings, like reference numbers generally indicate identical, functionally similar, and/or structurally similar elements.

SUMMARY AND BRIEF DESCRIPTION

Figure 1:
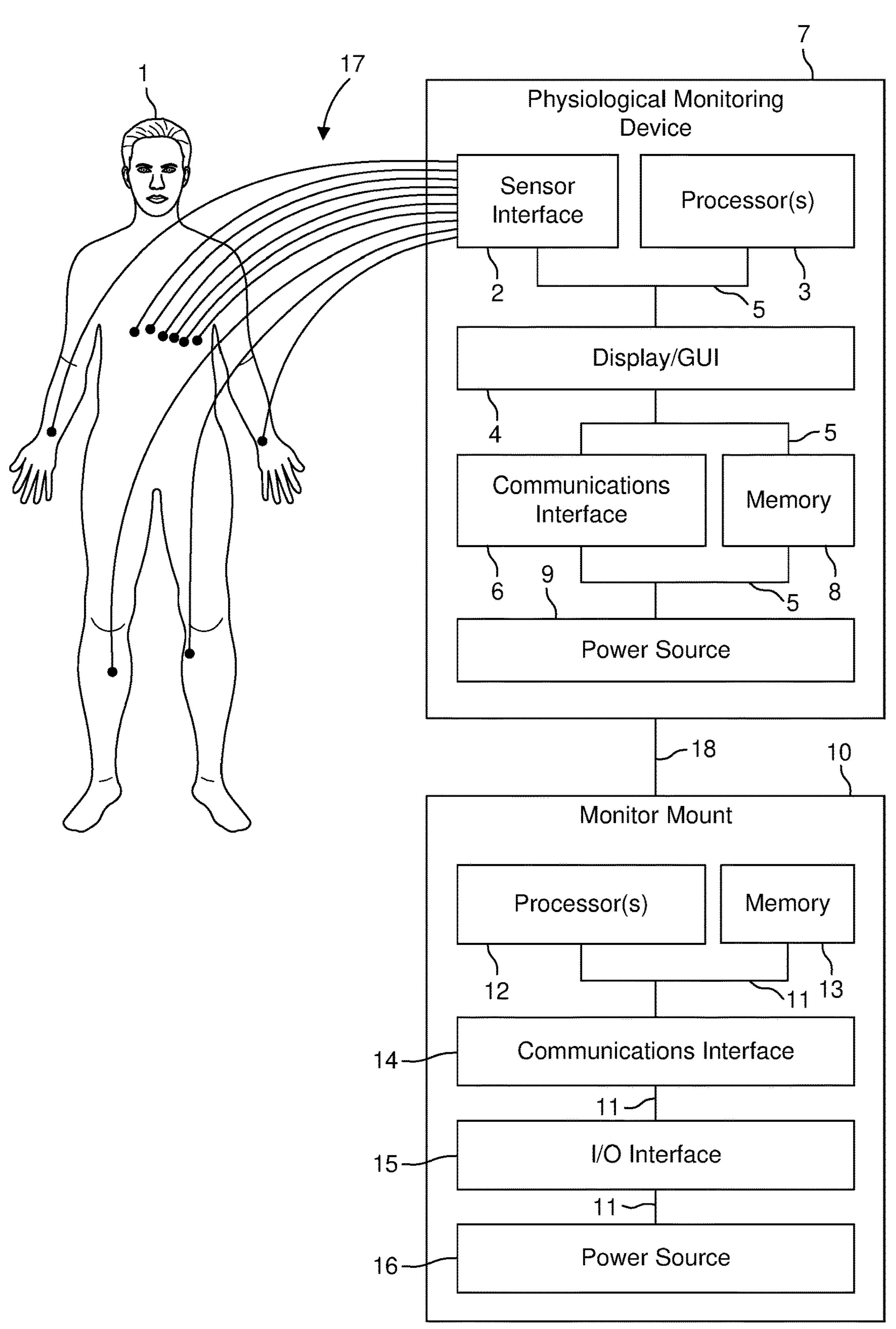
FIG. 1 is a schematic diagram of an exemplary physiological monitoring system for pace pulse detection according to one embodiment of the present disclosure.

To resolve at least one or more of the above problems and potentially other present or future problems, the present disclosure provides a method and apparatus for more accurate pace pulse detection. The apparatus includes one or more processors, and a computer-readable medium storing instructions that when executed by the one or more data processors, performs operations including receiving a plurality of sample signals from one electrocardiogram (ECG) lead, measuring a first-level noise of the plurality of sample signals during a first time interval, measuring a second-level noise of the plurality of sample during a second time interval, wherein the second time interval is different from the first time interval, generate one or more dynamic thresholds based on at least one of the measured first-level noise and the second-level noise, and detecting, based on the one or more dynamic thresholds, at least one of a start point, a peak point and an endpoint of the pace pulse signal from the plurality of sample signals. In one embodiment, the apparatus includes a physiological monitoring device.

The present disclosure also provides a method for detecting a pace pulse signal from an electronic pacemaker. The method includes receiving a plurality of sample signals from one electrocardiogram (ECG) lead, measuring a first-level noise of the plurality of sample signals during a first time interval, measuring a second-level noise of the plurality of sample during a second time interval, wherein the second time interval is different from the first time interval, generating one or more dynamic thresholds based on at least one of the measured first-level noise and the second-level noise, and detecting, based on the one or more dynamic thresholds, at least one of a start point, a peak point and an endpoint of the pace pulse signal from the plurality of sample signals.

Additionally, the present disclosure provides a computer program on a non-transitory computer readable medium comprising the steps of receiving a plurality of sample signals from one electrocardiogram (ECG) lead, measuring a first-level noise of the plurality of sample signals during a first time interval, measuring a second-level noise of the plurality of sample during a second time interval, wherein the second time interval is different from the first time interval, generating one or more dynamic thresholds based on at least one of the measured first-level noise and the second-level noise, and detecting, based on the one or more dynamic thresholds, at least one of a start point, a peak point and an endpoint of the pace pulse signal from the plurality of sample signals.

DETAILED DESCRIPTION

The following detailed description is made with reference to the accompanying drawings and is provided to assist in a comprehensive understanding of various example embodiments of the present disclosure. The following description includes various details to assist in that understanding, but these are to be regarded as merely examples. Accordingly, those of ordinary skill in the art will recognize that various changes and modifications of the examples described herein can be made without departing from the spirit and scope of the present disclosure. In addition, descriptions of well-known functions and constructions may be omitted for clarity and conciseness.

For example, in the description of the figures that follow, the automatic power on apparatus, system, method, and circuit are implemented in patient monitors. However, it should be understood and appreciated by one of ordinary skill in the art that the automatic power on apparatus, system, method, and circuit of the present disclosure can be implemented in other medical or electronic devices. The implementation of the automatic power on apparatus, system, method, and circuit in the patient monitors is meant only to assist in the understanding of the present disclosure and in no way is meant to limit the implementation the automatic power on apparatus, system, method, and circuit described herein.

Additionally, the terms and words used in the following description and claims are not limited to the bibliographical meanings, but are merely used to enable a clear and consistent understanding of the present disclosure. Accordingly, it should be apparent to those skilled in the art that the following description of the present disclosure is provided for illustration purposes only, and not for the purpose of limiting the present disclosure as defined by the appended claims and their equivalents.

FIG. 1 is a schematic diagram of an exemplary physiological monitoring system for pace pulse detection. As shown in FIG. 1, the system includes a physiological monitoring device 7 capable of receiving physiological data from various sensors 17 connected to a patient 1, and a monitor mount 10 to which the physiological monitoring device 7 is removably mounted or docked.

In general, it is contemplated by the present disclosure that the physiological monitoring device 7 and the monitor mount 10 include electronic components or electronic computing devices operable to receive, transmit, process, store, and/or manage patient data and information associated performing the functions of the system, which encompasses any suitable processing device adapted to perform computing tasks consistent with the execution of computer-readable instructions stored in a memory or a computer-readable recording medium.

Further, any, all, or some of the computing devices in the physiological monitoring device 7 and the monitor mount 10 may be adapted to execute any operating system, including Linux, UNIX, Windows Server, etc., as well as virtual machines adapted to virtualize execution of a particular operating system, including customized and proprietary operating systems. The physiological monitoring device 7 and the monitor mount 10 are further equipped with components to facilitate communication with other computing devices over one or more network connections, which may include connections to local and wide area networks, wireless and wired networks, public and private networks, and any other communication network enabling communication in the system.

As shown in FIG. 1, the physiological monitoring device 7 is, for example, a patient monitor implemented to monitor various physiological parameters of the patient 1 via the sensors 17. The physiological monitoring device 7 includes a sensor interface 2, one or more processors 3, a display/GUI 4, a communications interface 6, a memory 8, and a power source 9. The sensor interface 2 can be implemented in software or hardware and used to connect via wired and/or wireless connections to one or more physiological sensors and/or medical devices 17 for gathering physiological data from the patient 1.

The data signals from the sensors 17 include, for example, data related to an electrocardiogram (ECG), non-invasive peripheral oxygen saturation (SpO2), non-invasive blood pressure (NIBP), temperature, and/or tidal carbon dioxide (etCO2), apnea detection, and other similar physiological data. The one or more processors 3 are used for controlling the general operations of the physiological monitoring device 7. Each one of the one or more processors 3 can be, but are not limited to, a central processing unit (CPU), a hardware microprocessor, a multi-core processor, a single core processor, a field programmable gate array (FPGA), a microcontroller, an application specific integrated circuit (ASIC), a digital signal processor (DSP), or other similar processing devices capable of executing any type of instructions, algorithms, or software for controlling the operation and performing the functions of the physiological monitoring device 7.

The display/GUI 4 is for displaying various patient data and hospital or patient care information and includes a user interface implemented for allowing communication between a user and the physiological monitoring device 7. The display/GUI 4 includes, but is not limited to, a keyboard, a liquid crystal display (LCD), cathode ray tube (CRT), thin film transistor (TFT), light-emitting diode (LED), high definition (HD) or other similar display devices with touch screen capabilities. The patient information displayed can, for example, relate to the measured physiological parameters of the patient 1 (e.g., blood pressure, heart related information, pulse oximetry, respiration information, etc.) as well as information related to the transporting of the patient 1 (e.g., transport indicators).

The communications interface 6 allows the physiological monitoring device 7 to directly or indirectly (via, for example, the monitor mount 10) to communicate with one or more computing networks and devices. The communications interface 6 can include various network cards, interfaces or circuitry to enable wired and wireless communications with such computing networks and devices. The communications interface 6 can also be used to implement, for example, a Bluetooth connection, a cellular network connection, and/or a WiFi connection. Other wireless communication connections implemented using the communications interface 6 include wireless connections that operate in accordance with, but are not limited to, IEEE 802.11 protocol, a Radio Frequency for Consumer Electronics (RF4CE) protocol, ZigBee protocol, and/or IEEE 802.15.4 protocol.

Additionally, the communications interface 6 can enable direct (i.e., device-to-device) communications (e.g., messaging, signal exchange, etc.) such as from the monitor mount 10 to the physiological monitoring device 7 using, for example, a USB connection. The communications interface 6 can also enable direct device-to-device connection to other devices such as to a tablet, PC, or similar electronic device; or to an external storage device or memory.

The memory 8 can be a single memory or one or more memories or memory locations that include, but are not limited to, a random access memory (RAM), a memory buffer, a hard drive, a database, an erasable programmable read only memory (EPROM), an electrically erasable programmable read only memory (EEPROM), a read only memory (ROM), a flash memory, hard disk or any other various layers of memory hierarchy. The memory 8 can be used to store any type of instructions and patient data associated with algorithms, processes, or operations for controlling the general functions and operations of the physiological monitoring device 7.

The power source 9 can include a self-contained power source such as a battery pack and/or include an interface to be powered through an electrical outlet (either directly or by way of the monitor mount 10). The power source 9 can also be a rechargeable battery that can be detached allowing for replacement. In the case of a rechargeable battery, a small built-in back-up battery (or super capacitor) can be provided for continuous power to be provided to the physiological monitoring device 7 during battery replacement. Communication between the components of the physiological monitoring device 7 (e.g., 2, 3, 4, 6, 8, and 9) are established using an internal bus 5.

As shown in FIG. 1, the physiological monitoring device 7 is connected to the monitor mount 10 via a connection 18 that establishes a communication connection between, for example, the respective communications interfaces 6, 14 of the devices 7, 10. The connection 18 enables the monitor mount 10 to detachably secure the physiological monitoring device 7 to the monitor mount 10. In this regard, "detachably secure" means that the monitor mount 10 can secure the physiological monitoring device 7, but the physiological monitoring device 7 can be removed or undocked from the monitor mount 10 by a user when desired. The connection 18 may include, but is not limited to, a universal serial bus (USB) connection, parallel connection, a serial connection, coaxial connection, a High-Definition Multimedia Interface (HDMI) connection, or other similar connection known in the art connecting to electronic devices.

The monitor mount 10 includes one or more processors 12, a memory 13, a communications interface 14, an I/O interface 15, and a power source 16. The one or more processors 12 are used for controlling the general operations of the monitor mount 10. Each one of the one or more processors 12 can be, but are not limited to, a central processing unit (CPU), a hardware microprocessor, a multi-core processor, a single core processor, a field programmable gate array (FPGA), a microcontroller, an application specific integrated circuit (ASIC), a digital signal processor (DSP), or other similar processing device capable of executing any type of instructions, algorithms, or software for controlling the operation and performing the functions of the monitor mount 10.

The memory 13 can be a single memory or one or more memories or memory locations that include, but are not limited to a random access memory (RAM), a memory buffer, a hard drive, a database, an erasable programmable read only memory (EPROM), an electrically erasable programmable read only memory (EEPROM), a read only memory (ROM), a flash memory, hard disk or any other various layers of memory hierarchy. The memory can be used to store any type of instructions associated with algorithms, processes, or operations for controlling the general functions and operations of the monitor mount 10.

The communications interface 14 allows the monitor mount 10 to communicate with one or more computing networks and devices (e.g., the physiological monitoring device 7). The communications interface 14 can include various network cards, interfaces or circuitry to enable wired and wireless communications with such computing networks and devices. The communications interface 14 can also be used to implement, for example, a Bluetooth connection, a cellular network connection, and a WiFi connection. Other wireless communication connections implemented using the communications interface 14 include wireless connections that operate in accordance with, but are not limited to, IEEE 802.11 protocol, a Radio Frequency For Consumer Electronics (RF4CE) protocol, ZigBee protocol, and/or IEEE 802.15.4 protocol.

The communications interface 14 can also enable direct (i.e., device-to-device) communications (e.g., messaging, signal exchange, etc.) such as from the monitor mount 10 to the physiological monitoring device 7 using, for example, a USB connection, coaxial connection, or other similar electrical connection. The communications interface 14 can enable direct (i.e., device-to-device) to other device such as to a tablet, PC, or similar electronic device; or to an external storage device or memory.

The I/O interface 15 can be an interface for enabling the transfer of information between monitor mount 10, one or more physiological monitoring devices 7, and external devices such as peripherals connected to the monitor mount 10 that need special communication links for interfacing with the one or more processors 12. The I/O interface 15 can be implemented to accommodate various connections to the monitor mount 10 that include, but is not limited to, a universal serial bus (USB) connection, parallel connection, a serial connection, coaxial connection, a High-Definition Multimedia Interface (HDMI) connection, or other known connection in the art connecting to external devices.

The power source 16 can include a self-contained power source such as a battery pack and/or include an interface to be powered through an electrical outlet (either directly or by way of the physiological monitoring device 7). The power source 16 can also be a rechargeable battery that can be detached allowing for replacement. Communication between the components of the monitor mount 10 (e.g., 12, 13, 14, 15 and 16) are established using an internal bus 11.

It should be understood by one of ordinary skill in the art that the present disclosure may be implemented by any combination of an apparatus, a system, an integrated circuit, and a computer program on a non-transitory computer readable recording medium. The one more processors 3, 12 may be implemented as an integrated circuit (IC), an application specific integrated circuit (ASIC), or large-scale integrated circuit (LSI), system LSI, super LSI, or ultra LSI components which perform a part or all of the functions described in the present disclosure.

Figure 2:
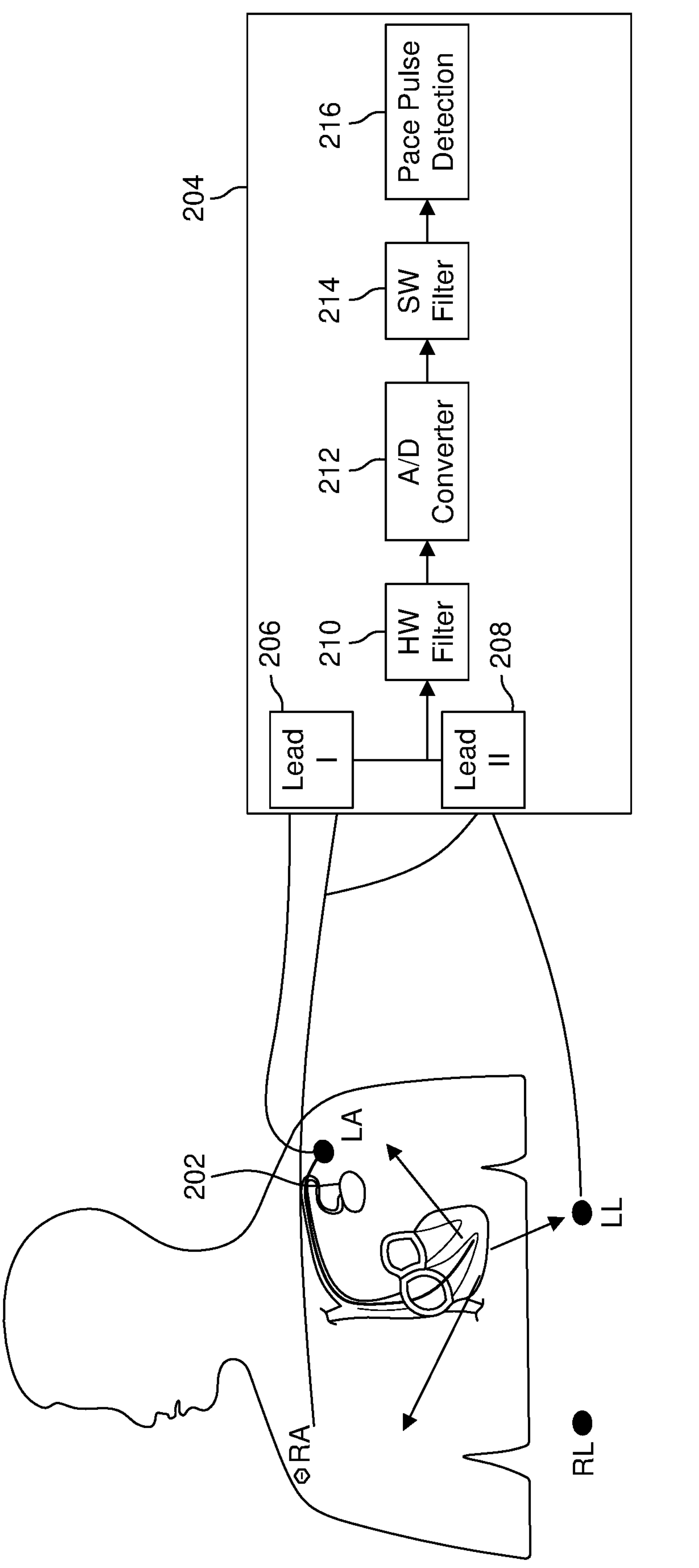
FIG. 2 is a schematic diagram of an exemplary physiological monitoring system with a plurality of surface ECG leads for detecting pace pulse generated by a pacemaker implanted in a patient according to one embodiment of the present disclosure.

FIG. 2 illustrates an exemplary physiological monitoring system with a plurality of surface ECG electrodes for detecting pace pulse generated by a pacemaker 202 implanted in a patient. The pacemaker 202 generates pace pulses that stimulate heart muscle, where the pulse signal is attenuated by the patient body and sensed by a plurality of ECG electrodes attached to predetermined positions on the surface of the patient body (e.g., Left Arm=LA, Right Arm=RA, Left Leg=LL and Right Leg=RL). As illustrated, two electrodes attached to RA and LA respectively, are connected to the patient monitor via the sensor interface 206 and configured to measure electrical potential signal of the heart from a first vector (lead I). Similarly, two electrodes attached to RA and LL respectively, are connected to the patient monitor via the sensor interface 208 for ECG signal measurement from a second vector (lead II). The signals from two ECG leads are filtered using hardware filters 210 (e.g., high-pass and/or low-pass filters), converted to digital forms using ND converter 212, and further filtered using software filtering strategies 214 (e.g., low-pass filters). The sampling rate for the conversion may be 10,000-100,000 samples per second (sps). In one embodiment of the present disclosure, the sample rate for conversion may be 15,000-30,000 sps. Subsequently, the digital data stream is passed for pace pulse detection 216, which will be described in more detail as follows. The sampling rate used in the pace pulse detection process is preferably 10,000-100,000 sps but could optionally be as low as 5,000 sps.

In one embodiment, the pace pulse detection as described below may be performed on the measured signals from a single ECG lead. In another embodiment, the pace pulse detection may be performed on more than one ECG lead (e.g., Lead I and Lead II). Performing pace pulse detection process on multiple ECG leads may further improve detection sensitivity by e.g., identifying pulse signals with very small amplitude and narrow width. Furthermore, it may improve detection specificity by rejecting noise.

Figure 3:
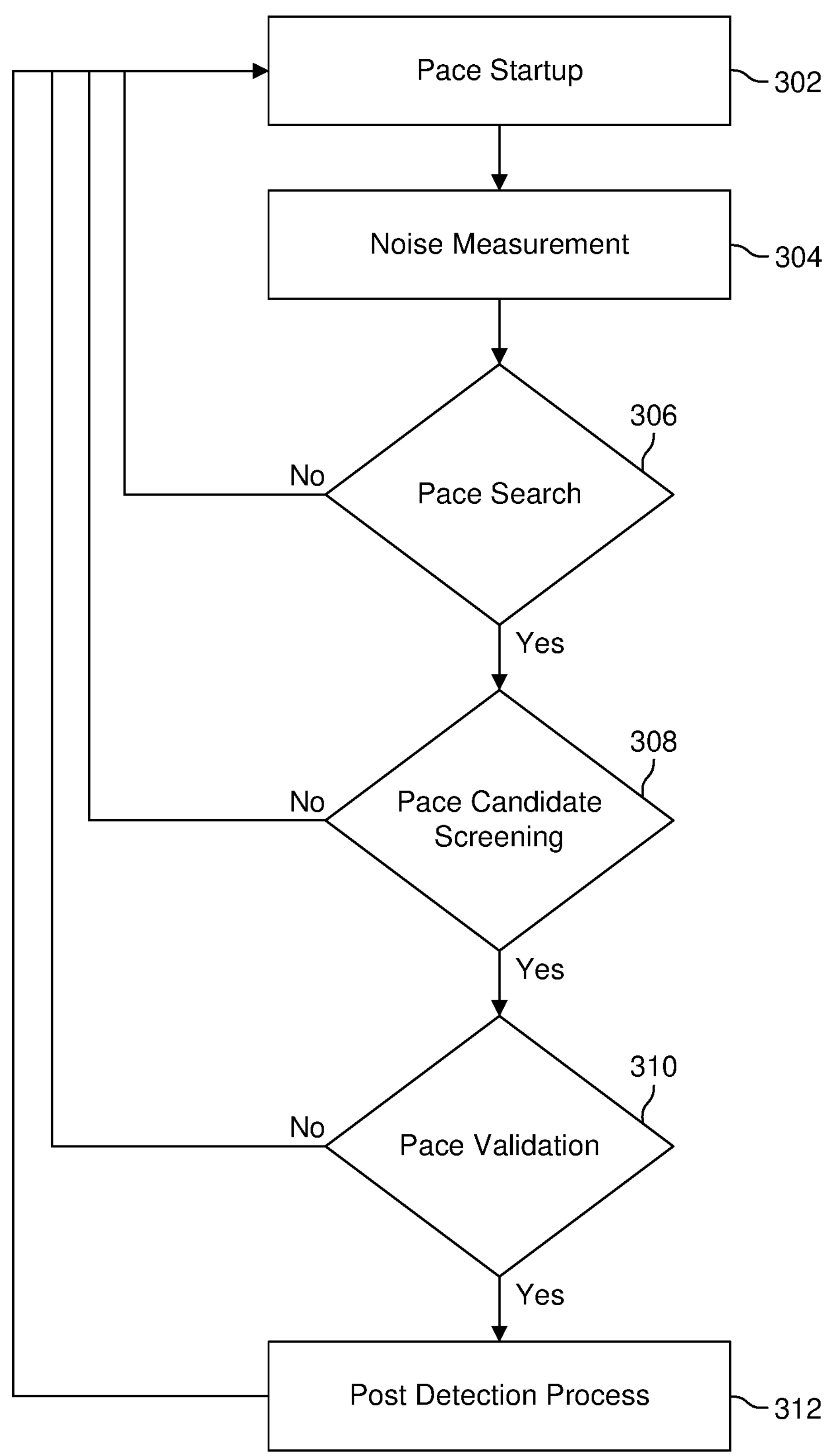
FIG. 3 is a flow diagram of an exemplary pace pulse detection process according to one embodiment of the present disclosure.
Figure 4:
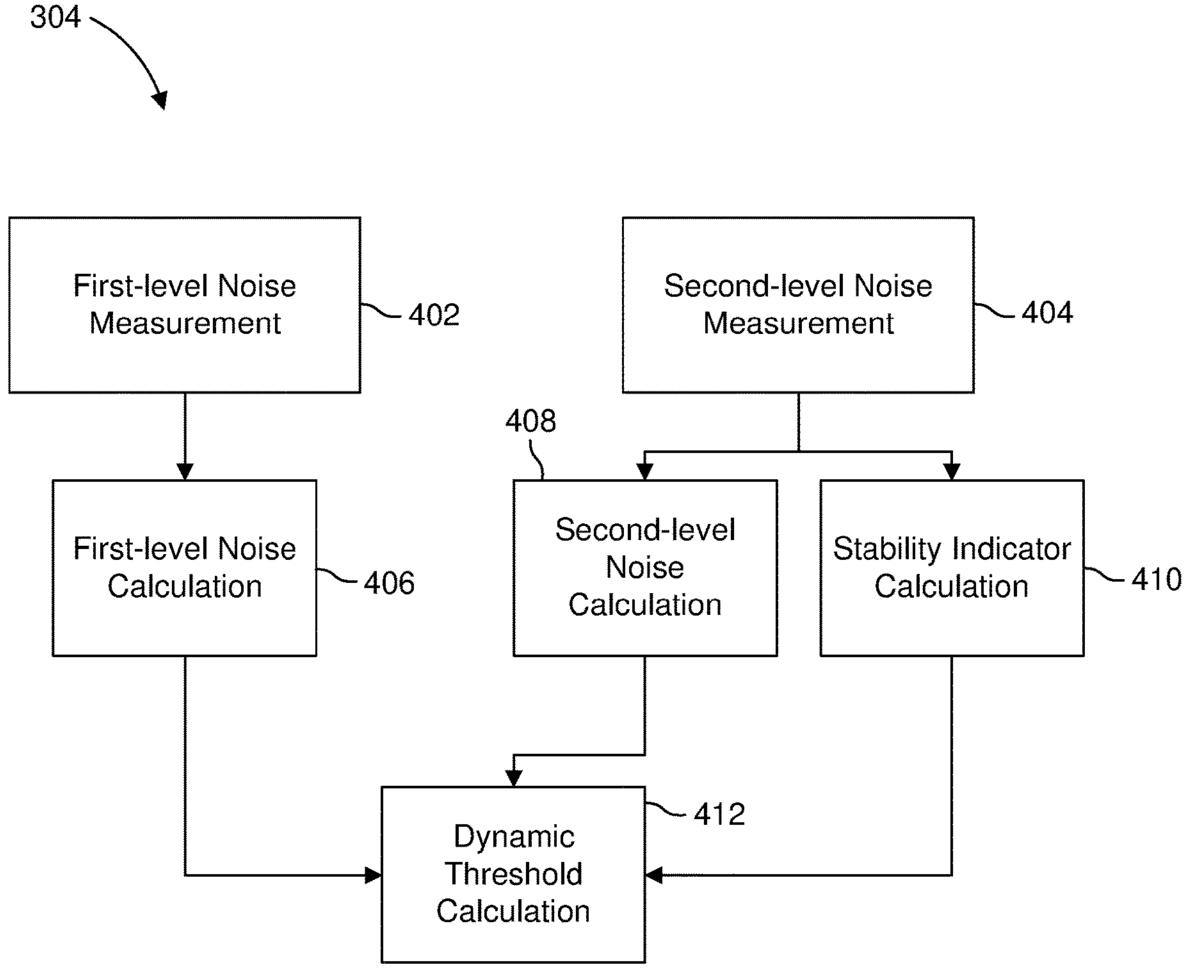
FIG. 4 is a flow diagram of an exemplary noise detection process according to one embodiment of the present disclosure.

FIG. 3 is a flow diagram of an exemplary pace pulse detection process according to one embodiment of the present disclosure. The exemplary pace pulse detection process includes multiple steps. After a pace pulse starts at step 302, the baseline noise is measured at step 304. In one embodiment of the present disclosure as illustrated in FIG. 4, the noise measurement step 304 may include a two-level noise measurement process, based on which one or more threshold values are generated dynamically. Generated "dynamically" means that the applicable threshold values are recalculated on an ongoing basis. For example, each dynamic threshold could be recalculated for each sample signal or could be recalculated periodically (e.g., every 50 sample signals).

When the baseline noise level and dynamic threshold values are determined, the pace search step 306 occurs. In one embodiment, the sample signal may be analyzed for edge detection and by comparing with the dynamic threshold values, the sample signal may be determined as an edge point of a pace pulse signal. For example, a sample signal may be analyzed for a plurality of edge points based on the morphology of the waveform, including start point (S), peak point (P), tail point (T) and endpoint (E). The portion of the waveform starting with a start point (S) and ending with an endpoint (E) may be referred to herein as a candidate segment, meaning a series of sampled data points that form a possible pace pulse signal.

In one embodiment, a difference in absolute value of a most recent sample signal with an earlier sample signal (e.g., a second most recent sample signal) may be compared with one or more startup thresholds dynamically generated in noise measurement step 304. When the difference exceeds the one or more startup thresholds, the most recent sample signal may be identified as a start point S.

In another embodiment, a difference in absolute value of a most recent sample signal with baseline noise (e.g., calculated from at least one of first-level noise and second-level noise) may be compared with an amplitude threshold dynamically generated in noise measurement step 304. When the difference exceeds the amplitude threshold, the most recent sample signal may be identified as a peak point (−P), that is, an edge point that has a largest amplitude within one pace pulse.

If one or more sample signals exceed the dynamic thresholds and are identified as edge points of a pace pulse, the pace pulse candidate is found (Y in step 306). If not, the sample signal is identified as non-pace pulse and the pace pulse detection process will restart for the next round (N in step 306).

A pace pulse candidate is further screened at step 308. In one embodiment, the morphology of the waveform of the candidate may be analyzed for at least one of the features including symmetry, amplitude, width, start slope, end slope. For example, the waveform of the candidate may be analyzed for symmetry, since pacemakers commonly generate electronic pulse signals with a symmetric square-shaped waveform. The amplitude of the signal may be compared with the amplitude threshold dynamically generated based on the noise level. If the pace pulse candidate exceeds one or more thresholds, it is further validated at pace validation step 310 (Y in step 308). If not, the sample signal is identified as non-pace pulse signal (N in step 308). In another embodiment, the pace candidate screening step 308 may be integrated as a part of the pace search step 306.

At pace validation step 310, different sample signals collected from a same ECG lead or from different ECG leads are compared and validated. In one embodiment, sample signals generated in a same time window from different ECG leads (e.g., lead I and II as illustrated in FIG. 2) may be cross-checked. In another embodiment, a sample signal generated from a single ECG lead may be compared with a template stored in the physiological monitoring device, where the template includes one or more previously validated pace pulses measured on the same ECG lead.

Figure 7:
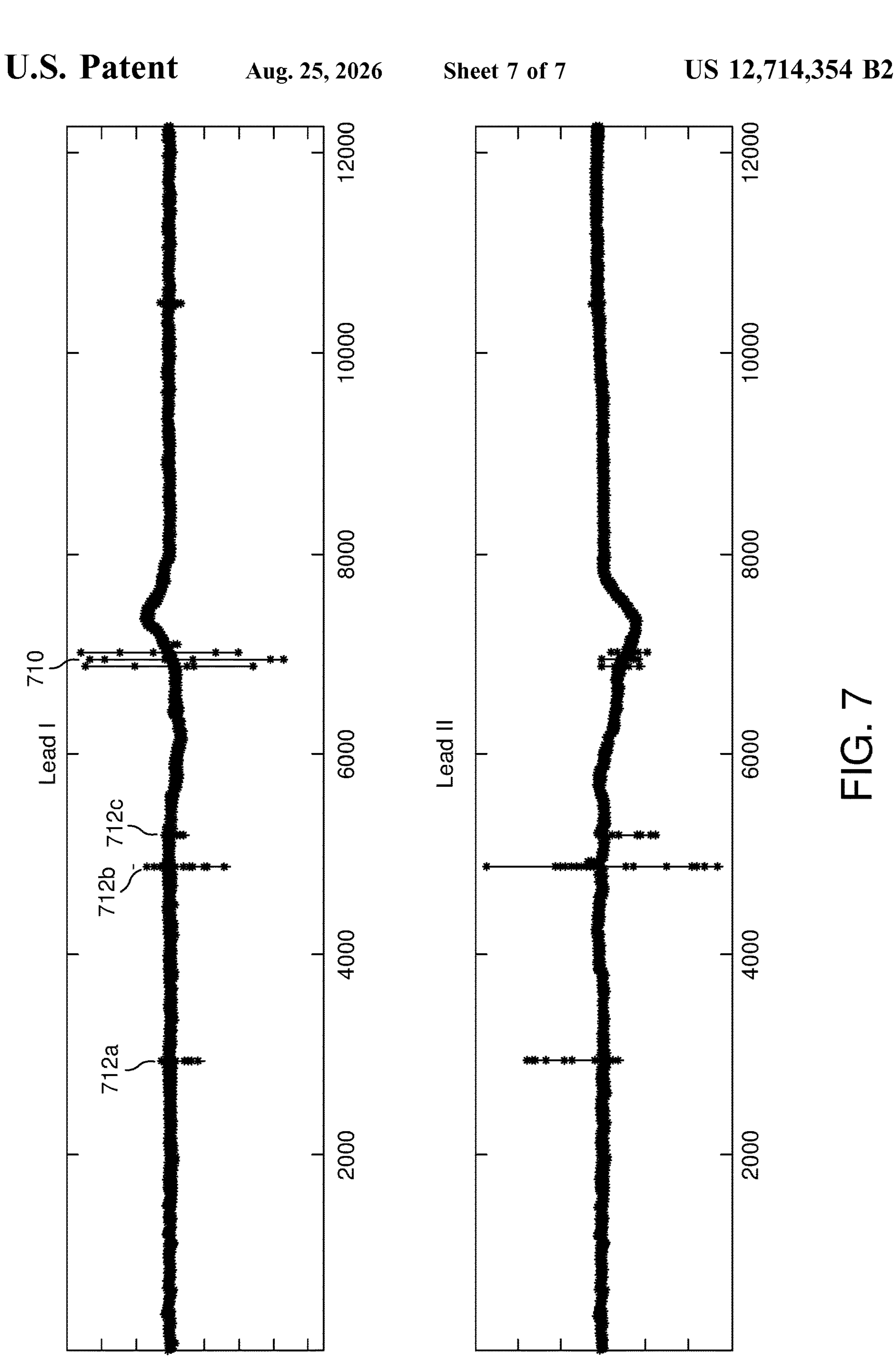
FIG. 7 is a graph showing ECG signals from two different ECG leads.

To further improve the specificity and accuracy of the pace pulse detection, the validation step 310 may further include high-frequency noise check. An example of a high-frequency noise pulse 710 is shown in FIG. 7, along with three example pace pulse signals 712*a-c*. High-frequency noise pulses often exhibit a relatively narrow pulse width and/or a large pulse area. For example, if a sample signal has an area that is 10 times the area of any of the stored template signals (or a predefined pace pulse area) and the width of the sample signal is less then have of the width of any of the stored sample signals (or a predefined pace pulse signal width), the sample signal is identified as a non-pace pulse signal.

In addition, one or more conditions including physiological change of the patient and device features from different pacemakers may also be checked in the validation step 310, since these conditions cause untypical signal changes that are not easily identified when compared with a pace pulse template. The validation step 310, as further illustrated in FIG. 6, will be described in detail below.

If the signal is validated (Y in step 310), it enters post detection process 312. In one embodiment, the validated pace pulse signal may be stored in a template datastore of the physiological monitoring device and update the template database. The validated signal may be added as a newly-generated template to the existing template database. Alternatively, it may be integrated with previously-stored template to create an updated template or substitute an old template. The updated template database is used for future pace pulse validation.

In another embodiment, validated pace pulses may be stored as a plurality of templates and classified depending on the pacemaker lead type where a pulse signal is generated and/or the types of pacing. For a multipoint pacing device, for example, the validated pace pulses may be stored and classified as one of right atrium (RA) pulse, right ventricle (RV) pulse, left ventricle (LV) pulse.

FIG. 4 is a flow diagram of an exemplary noise measurement process according to one embodiment of the present disclosure. The noise measurement may further include multi-level noise measurement. As illustrated in FIG. 4, the noise measurement process 304 may include a first-level noise measurement 402 and a second-level noise measurement 404, where the two-level noise measurements may occur concurrently or sequentially. In one embodiment, the first-level noise measurement 402 may include first-level noise calculation 406 by comparing a plurality of sample signals during a pre-determined time interval. For example, a range of such as from about 10 to about 100 sample signals during a 0.5-10 millisecond (ms) interval may be compared, and a difference between a minimum value and a maximum value may be determined as a first-level noise. For example, the first-level noise measurement may occur every 50 sample signals during an interval of approximately from about 3 to about 5 ms. The time interval may be calculated as a time duration retrospectively from a most recent sample signal to earlier sample signals.

In one embodiment, the noise measurement process 304 may further include a second-level noise measurement 404 by comparing a plurality of sample signals during a pre-determined time interval. The interval used in the second-level noise measurement 404 may be different from the one used in the first-level noise measurement 402. In one embodiment, a range of such as from about 100 to about 500 sample signals during an about 5 to about 50 ms interval may be compared, and a difference between a minimum and a maximum value may be determined as a second-level noise (shown as second-level noise calculation 408 in FIG. 4). In another embodiment, the second-level noise measurement may occur every 300 sample signals during an interval of approximately about 18 to about 30 ms. The interval may be calculated as a time duration from a most recent sample signal to earlier sample signals.

The second-level noise measurement 408 may be repeated in a pre-determined manner. In one embodiment, the second-level noise calculation 408 may occur every 300 sample signals during an interval of approximately 20 ms, and obtain a peak-to-peak second-level noise by calculating a difference between a minimum value and a maximum value during this 20 ms interval. This process may be repeated to calculate second-level noise in one or more earlier time windows. For example, in a time window of 500 ms retrospectively from a most recent sample signal to earlier sample signals, the second-level noise calculation 408 may be repeated for 25 times, where each time of calculation 408 based on the 20 ms time interval may calculate a second-level noise in the corresponding time window (also referred to herein as a time block).

A list of the plurality of second-level noise values may be ranked and based on the ranking, an updated second-level noise value and/or a stability indicator may further be calculated (410 shown in FIG. 4). In one embodiment, the second-level noise calculation may be consecutively performed based on a 20 ms time interval and repeated for 25 times in a 500 ms time window. Each time the calculation is completed, the obtained noise values within the 500 ms time window may be re-ranked. Accordingly, an updated second-level noise may be determined as a medium point of the ranked noise values. Optionally, a stability indicator may also be calculated, for example, as a difference between a minimum value and the medium of the re-ranked noise values. The stability indicator could be binary, with a one indicating a relatively unstable noise level and a zero indicating a relatively stable noise level. Alternatively, the stability indicator could be a value that is calculated and is a more granular indication of noise stability.

Accordingly, at least one of the calculated first-level noise, second-level noise, and stability indicator may be utilized to determine one or more dynamic thresholds used for subsequent pace search step 306 and/or pace candidate screening step 308 (412 in FIG. 4). The calculated dynamic threshold values may include a startup threshold, one or more slope thresholds (e.g., a start-slope threshold and an end-slope threshold), and an amplitude threshold. In one embodiment, a physiological monitoring device may include a database for determining one or more dynamic thresholds, where the database includes at least one pre-determined threshold range for each of first-level noise, second-level noise, and stability indicator. The database also includes a list of dynamic thresholds, each of the dynamic thresholds corresponds to a pre-determined threshold range for first-level noise, second-level noise, and stability indicator. When each of the calculated first-level noise, second-level noise, and/or stability indicators is compared to its corresponding pre-determined threshold range, a dynamic threshold can be determined. For example, a startup threshold may be determined by comparing calculated second level noise and stability indicator with the corresponding pre-determined threshold range in the database, respectively. Optionally, a startup threshold may be determined by comparing the calculated first level noise and second level noise with its corresponding pre-determined threshold range in the database, respectively. In addition, a start-slope threshold may be determined by comparing the calculated first level noise, second level noise and stability indicator with its corresponding pre-determined threshold range in the database, respectively. When at least one of first-level noise, second-level noise, and stability indicator is updated in real time as described above, the determination process of dynamic threshold is repeated to reflect the update in the noise measurement process. The startup threshold and/or slope thresholds may be used to compare with a sample signal and determine a start point S in edge detection. The amplitude threshold may be used to determine a peak point P in edge detection.

The multi-level noise measurement according to the embodiments in the present disclosure provides advantages including improvements in detection sensitivity. By calculating noise on a two-level basis, for example, using different time intervals and updating noise values by ranking, the two-level noises and stability indicator are updated in real time. Based on such, the thresholds determined based on the baseline noise are dynamically generated and to be used in a pace search step, which may capture pace pulses with a small amplitude.

Figure 5:
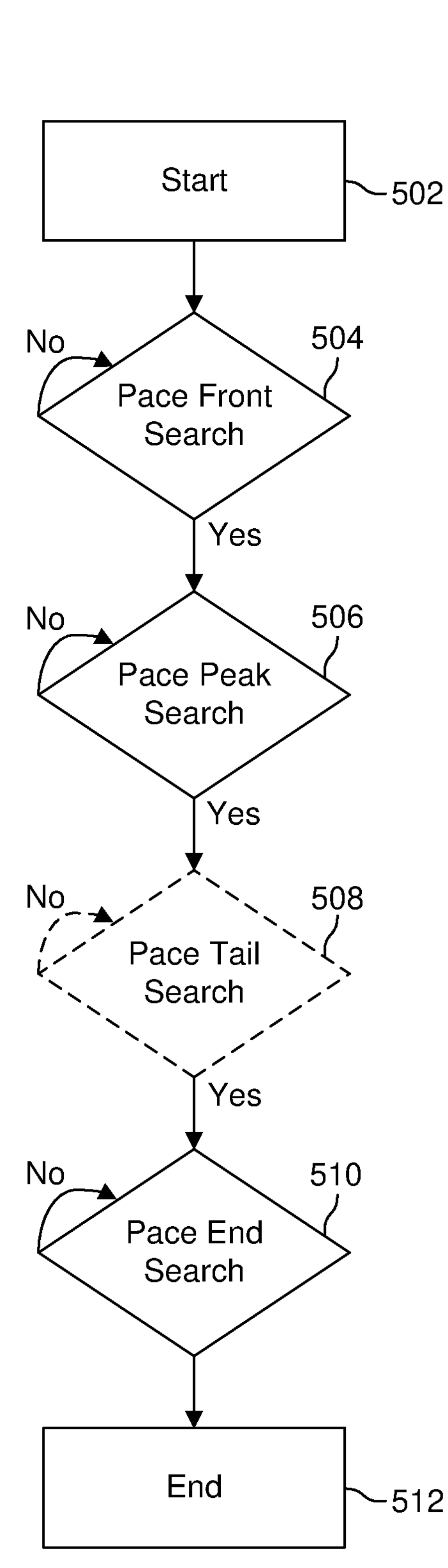
FIG. 5 is a flow diagram of an exemplary pace search process according to one embodiment of the present disclosure.

FIG. 5 is a flow diagram of an exemplary pace search process according to one embodiment of the present disclosure. Concurrently with or after the noise measurement step 304, the generated dynamic thresholds, individually or in any combination, is used in pace search step 306. Electronic pacemakers generate electronic stimulates, namely, pulses. Accordingly, a square-shaped wave form with a narrow width will be identified as a pace pulse. For each sample signal, the pace search step 306 determines whether it is a pace pulse candidate.

A sample signal may be analyzed for edge detection during step 306. In more detail, the process is initiated as step 502. Accordingly, it may further include pace front search 504, pace peak search 506, optionally pace tail search 508, and pace end search 510. By comparing with the dynamic thresholds, the sample signal may be determined as one of the edge points including start point S, peak point P, tail point T and endpoint E. In one embodiment, a most recent sample signal may be compared with a second most recent sample signal (e.g., approximately 50-100 microsecond (μs) earlier). The difference in absolute value between the two sample signals may be compared with a dynamic threshold (e.g., startup threshold) to determine a start point S of the waveform. Alternatively or additionally, a most recent sample signal may be compared with one or more earlier sample signals (e.g., approximately 100-500 μs earlier). In another embodiment, a plurality of dynamic thresholds including a startup threshold and a start slope threshold may be used in the pace front search 504. When the sample signal exceeds the dynamic thresholds and is identified as a start point S of the waveform, the peak search process starts to search for a next edge point (e.g., peak point P), as illustrated in step 506.

The pace peak search 506, pace tail search 508, and pace end search 510 may also use dynamic thresholds to identify edge points of a potential pace pulse. These search steps, individually or in any combination, may determine a pace pulse candidate. In one embodiment, three edge points (start point S, peak point P and endpoint E) are identified by exceeding corresponding dynamic thresholds, it may be determined as a pace pulse candidate. Otherwise, the signal is identified as non-pace pulse.

As illustrated in FIG. 3, to further improve the sensitivity and specificity of the pace pulse detection, the identified pace pulse candidate after the pace search step 306 may further be screened in pace candidate screening step 308. In one embodiment, one or more features in the morphology of the candidate may be analyzed. The features may include symmetry, slope direction, start slope (or onset slope), end slope (or offset slope), amplitude and width. For example, identified start slope and end slope may be analyzed for directions, where opposite directions indicate a true pace pulse. Furthermore, pulse width/amplitude may be measured and compared with minimum and/or maximum thresholds. These thresholds may be pre-determined or dynamically generated from noise measurement step 304. Optionally, the dynamic thresholds may further be configured so as to improve the specificity of the pace pulse detection. For example, the amplitude threshold used in pace candidate screening step 308 may be determined based on the measured first-level and second-level noise, and further adjusted to be slightly higher than the amplitude threshold used in pace search step 306.

Figure 6:
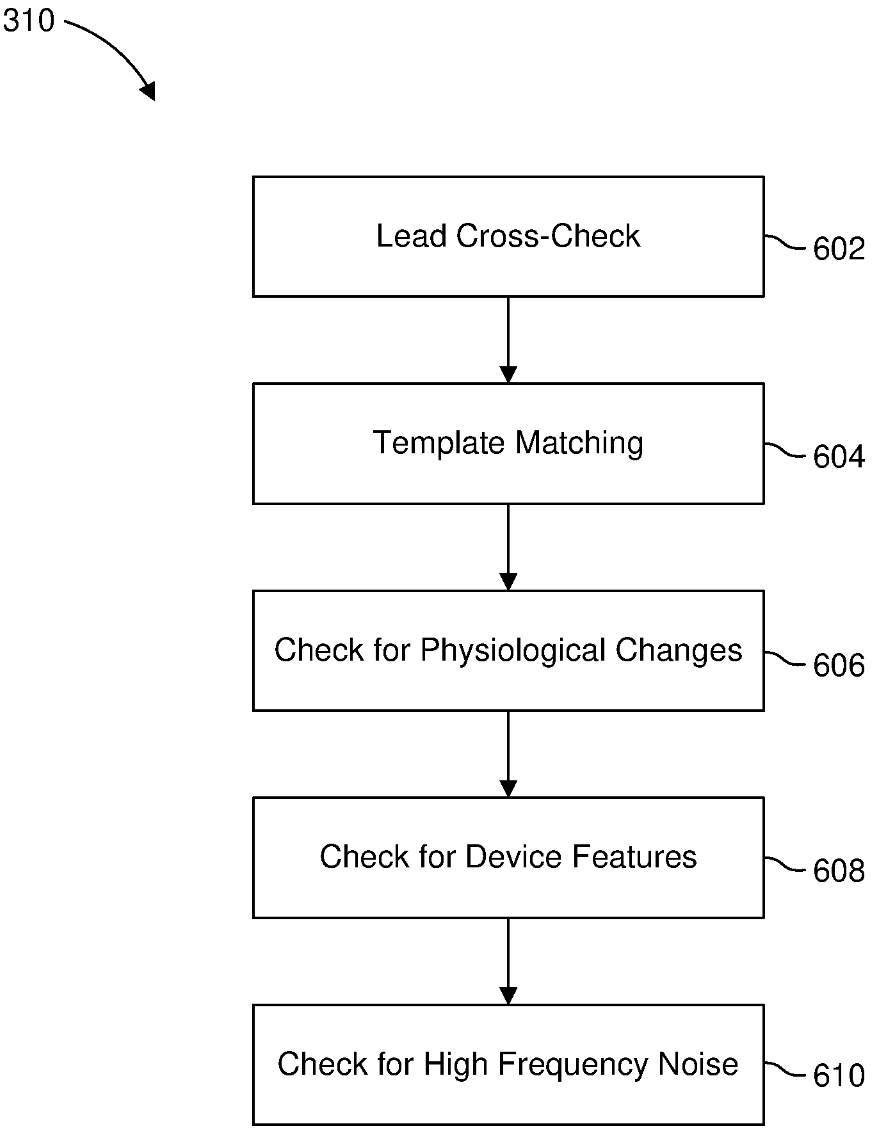
FIG. 6 is a flow diagram of an exemplary pace validation process according to one embodiment of the present disclosure.

FIG. 6 is a flow diagram of an exemplary pace validation process according to one embodiment of the present disclosure. The pace validation process may further include lead cross-check 602, template matching 604, physiological change check 606, device feature check 608 and high-frequency noise check 610. These validation steps, individually or in any combination, determines whether the pace pulse candidate is a true pace pulse generated from electronic pacemakers.

In one embodiment, the pace detection process may be performed on more than one ECG lead, for example, both Lead I and Lead II as illustrated in FIG. 2. As such, two pace pulse signals may be measured independently in a same time window. The two signals may be analyzed for edge detection, where the corresponding timestamps of one or more edge points (e.g., start point S, peak point P and endpoint E) may be checked for alignment. In an optional embodiment for detecting pace pulse generated by e.g., leadless pacemakers, the two pace pulse signals from two ECG leads may further be compared for peak direction, namely, whether the two pace pulse signals have a same peak direction.

In addition, the morphology of the waveforms may be compared between the signals from different leads. In one embodiment, pace pulse area of the pace pulse signal from different ECG leads may be calculated and compared to determine whether a difference ratio is below a certain threshold, for example, approximately 10-35%. In another embodiment, the pace pulse area may be calculated by summing absolute values of the difference between baseline and sample signals for the pace pulse, where the baseline may be relatively consistent throughout each pace pulse duration (approximately shorter than 3 ms). Each calculated pace pulse area may further be normalized for amplitude and compared.

During the template matching step 604, pace pulse signals measured from a same ECG lead may be validated. The physiological monitoring device may include a template datastore where previously validated pace pulse signals are stored and updated. In one embodiment, a most recent pace pulse candidate measured on an ECG lead may be compared with a corresponding template, including comparison in at least one of peak directions, width and pace pulse area. For example, when the sample signal has a same peak direction as the template, and/or a difference in absolute value between the sample width and the template width exceeds a threshold (e.g., lower than a minimum threshold), the pace pulse candidate may be validated. Another example is when a difference ratio between an area of the pace pulse candidate and an area of a corresponding template is below a certain threshold, for example, approximately 10-35%, the candidate is validated, where each pulse area is calculated by summing absolute values of difference between baseline and sample signals for the pace pulse. In one embodiment, each pace pulse area may be further normalized by width.

Depending on numbers and locations of pacing leads associated with pacemakers and different types of pacing, the present disclosure may store and classify plurality types of pace pulse templates. In one embodiment, a single type of template may be stored and classified as right atrium (RA) pulse or right ventricle (RV) pulse for single chamber pacing where a single lead is paced either at right atrium (upper chamber) or right ventricle (lower chamber). For multipoint pacing that requires two or more leads, multiple templates may be stored and classified as one of RA pulse, RV pulse and left ventricle (LV) pulse (including pulse at LV-lower region and/or LV-upper region). In another embodiment, the database may store and classify two templates for anti-tachycardia pacing, including RA pulse and RV pulse.

The validation step 310 according to one or more embodiments of the present disclosure may further include device physiological change check 606, feature check 608 and/or high-frequency noise check 610. These check steps, individually or in any combination, may further improve the specificity and accuracy for pace pulse detection.

Physiological changes of the patient wearing a pacemaker, for example, body position change, may cause pace pulse morphology change in surface ECG measurements. Furthermore, different generations of pacemakers from different manufacturers also provide varying device features (e.g., capture management feature provided by pacemakers that allows automatic adjustment of pacing amplitudes in response to changing pacing thresholds). In addition, different pacing types (e.g., anti-tachycardia pacing, ventricular safety pacing and post shock pacing) cause changes in the morphology of pace pulse signals, including width and/or amplitude. These changes may not be easily identified by template matching, which causes false negative. In one embodiment, the physiological change check 606 and/or device feature check 608 may establish one or more thresholds including width and area to compare with the pace pulse candidate, thereby determining whether it is a validated pace pulse. Optionally, different and/or additional types of checking steps and thresholds used in the checking steps may be used to be adapted with the features of the corresponding pacing type. For example, additional timestamp checks or higher thresholds (e.g., width, area, energy) may be performed.

It should be noted that one or more of the validation steps 602, 604, 606, 608 and 610 may be used, where the numbers and/or orders as described in the present disclosure are for exemplary purposes, and not intended to limit the scope of the disclosure. When a pace pulse candidate meets at least one of the thresholds in these validation steps, it may be validated as a pace pulse. For example, during lead cross-check 602, when two pace pulse signals generated from independent ECG leads are found to be matched, they may be validated. Alternatively, during template matching 604, when a sample signal measured on one lead is matched with a template, it may be validated. In another embodiment, the sample signal may meet two or more of the above checks in order to be validated as a pace pulse, otherwise it is rejected. Preferably, the criteria and thresholds discussed above that are used to determine whether each validation step has been met are preferably determined based on empirical data.

In contrast to the heart's electrical signal that typically falls between 0.05 to 100 Hz, a signal frequency range containing a pacemaker pulse falls between DC to 1.7 k Hz, which causes a much narrower pulse width of 0.2-2 milliseconds (ms). The amplitude of a pace pulse voltage is as low as a minimum range of 0.1-0.2 mV, which makes it challenging for the physiological monitoring device to identify pace pulse signals, especially considering the amplitude of the pace pulse voltage is close to or below the ground noise level of physiological monitoring devices in clinical applications. The described pace pulse detection apparatus and method according to the embodiments in the present disclosure provide a variety of advantages.

For example, the multi-level noise measurement step calculates baseline line noises in an accurate and real-time manner and generate multi-level noise values and/or stability indicator value, which may further be used to determine a plurality of dynamic threshold values. That is, the signal changes including noise level changes may be captured in a real-time basis and the thresholds may be dynamically adjusted in order to be used in pace search step and pace candidate screening step. As such, the sensitivity of the detection may be improved.

Furthermore, the validation process includes one or more check steps, with the consideration of physiological change of the patient and varying device features from different pacemakers. In addition, high-frequency noise is identified to reduce false positives. As such, the specificity and accuracy of the detection may be improved. The detection process may be applied in detecting pace pulses from different generations and types of pacemakers with varying device features. Further, artifacts caused by physiological change of the patient may also be identified.

The present disclosure may be implemented as a non-transitory computer-readable recording medium having recorded thereon a program embodying methods/algorithms for instructing the processor to perform the methods/algorithms. The non-transitory computer-readable recording medium can be, for example, a CD-ROM, DVD, Blu-ray disc, or an electronic memory device. For example, referring to FIG. 1, the programs or algorithms can be stored on a non-transitory computer-readable medium for causing a computer, such as the one or more processors 3, 12, to perform the steps or method described herein.

The computer programs, which can also be referred to as programs, software, software applications, applications, components, or code, include machine instructions for a programmable processor, and can be implemented in a high-level procedural language, an object-oriented programming language, a functional programming language, a logical programming language, or an assembly language or machine language. The term computer-readable recording medium refers to any computer program product, apparatus or device, such as a magnetic disk, optical disk, solid-state storage device, memory, and programmable logic devices (PLDs), used to provide machine instructions or data to a programmable data processor, including a computer-readable recording medium that receives machine instructions as a computer-readable signal.

Each of the elements of the present disclosure may be configured by implementing dedicated hardware or a software program on a memory controlling a processor to perform the functions of any of the components or combinations thereof. Any of the components may be implemented as a CPU or other processor reading and executing a software program from a recording medium such as a hard disk or a semiconductor memory or network or cloud based programs.

It is also contemplated that the implementation of the components of the present disclosure can be done with any newly arising technology that may replace any of the above implementation technologies.

By way of example, a computer-readable medium can comprise DRAM, RAM, ROM, EEPROM, CD-ROM or other optical disk storage, magnetic disk storage or other magnetic storage devices, or any other medium that can be used to carry or store desired computer-readable program code in the form of instructions or data structures and that can be accessed by a general-purpose or special-purpose computer, or a general-purpose or special-purpose processor. Disk or disc, as used herein, include compact disc (CD), laser disc, optical disc, digital versatile disc (DVD), floppy disk and Blu-ray disc where disks usually reproduce data magnetically, while discs reproduce data optically with lasers. Combinations of the above are also included within the scope of computer-readable media.

Use of the phrases "capable of," "capable to," "operable to," or "configured to" in one or more embodiments, refers to some apparatus, logic, hardware, and/or element designed in such a way to enable use of the apparatus, logic, hardware, and/or element in a specified manner. The subject matter of the present disclosure is provided as examples of apparatus, systems, methods, circuit, and programs for performing the features described in the present disclosure. However, further features or variations are contemplated in addition to the features described above. It is contemplated that the implementation of the components and functions of the present disclosure can be done with any newly arising technology that may replace any of the above implemented technologies.

Additionally, the above description provides examples, and is not limiting of the scope, applicability, or configuration set forth in the claims. Changes may be made in the function and arrangement of elements discussed without departing from the spirit and scope of the disclosure. Various embodiments may omit, substitute, or add various procedures or components as appropriate. For instance, features described with respect to certain embodiments may be combined in other embodiments.

Various modifications to the disclosure will be readily apparent to those skilled in the art, and the generic principles defined herein may be applied to other variations without departing from the spirit or scope of the present disclosure. Throughout the present disclosure the terms "example," "examples," or "exemplary" indicate examples or instances and do not imply or require any preference for the noted examples. Thus, the present disclosure is not to be limited to the examples and designs described herein but is to be accorded the widest scope consistent with the principles and novel features disclosed.

The invention claimed is:

1. A method for detecting a pace pulse signal, comprising:

receiving a plurality of sample signals from one electrocardiogram lead configured to be connected to a patient;

measuring a first-level noise of the plurality of sample signals during a first time interval by calculating a first difference between a first minimum value and a first maximum value of the plurality of sample signals during the first time interval;

measuring a second-level noise of the plurality of sample signals during a second time interval, the second time interval being different from the first time interval by calculating a second difference between a second minimum value and a second maximum value of the plurality of sample signals during the second time interval;

generating at least one dynamic threshold based on the measured first-level noise and the second-level noise; and based on the at least one dynamic threshold, detecting from the plurality of sample signals at least one of a start point, a peak point and an endpoint of the pace pulse signal.

2. The method according to claim 1, wherein detecting from the plurality of sample signals further comprises detecting a sample signal from the plurality of sample signals as the start point of the pace pulse signal when a difference in absolute value between the sample signal and an earlier sample signal exceeds the startup threshold.

3. The method according to claim 1, wherein the at least one dynamic threshold includes a startup threshold, a start-slope threshold, an end-slope threshold and an amplitude threshold.

4. The method according claim 1, further comprising calculating at least one of width and amplitude of the pace pulse signal.

5. The method according to claim 4, further comprising screening the pace pulse signal by comparing at least one of the width and amplitude of the pace pulse signal with the at least one dynamic threshold.

6. An apparatus for pace pulse detection comprising:

one or more processors; and a computer-readable medium storing instructions that, when executed by the one or more processors, performs operations comprising:

receiving a plurality of sample signals from each of at least one electrocardiogram, ECG, lead;

measuring a first-level noise of the plurality of sample signals during a first time interval, by calculating a difference between a first minimum value and a first maximum value of the plurality of sample signals during the first time interval;

measuring a second-level noise of the plurality of sample signals during a second time interval, the second time interval being different from the first time interval, by calculating a second difference between an second minimum value and a second maximum value of the plurality of sample signals during the second time interval;

generating at least one dynamic threshold based on the measured first-level noise and the second-level noise; and based on the at least one dynamic threshold, detecting from the plurality of sample signals at least one selected from the group of a start point, a peak point and an endpoint of the pace pulse signal.

7. The apparatus of claim 6, wherein the at least one dynamic threshold generated by the one or more processors includes a startup threshold, a start-slope threshold, an end-slope threshold and an amplitude threshold.

8. The apparatus of claim 7, wherein the operations performed by the one or more processors further comprise detecting a sample signal from the plurality of sample as the start point of the pace pulse signal when a difference in absolute value between the sample signal and an earlier sample signal exceeds the startup threshold.

9. The apparatus of claim 6, wherein the operations performed by the one or more processors further comprises:

calculating at least one of width and amplitude of the pace pulse signal and screening the pace; and pulse signal by comparing at least one of the width and amplitude of the pace pulse signal with the at least one dynamic threshold.

10. The apparatus of claim 6, wherein the operations performed by the one or more processors further comprises:

validating the pace pulse signal, wherein the pace pulse signal is validated when a difference ratio between an area of the pace pulse signal and an area of a template pace pulse exceeds a threshold; and storing the validated pace pulse signal, optionally wherein the pace pulse signal is validated when a difference ratio between an area of the pace pulse signal and an area of the template pace pulse exceeds a threshold, and further optionally wherein the template pace pulse includes at least one validated pace pulse signal.

11. The apparatus of claim 6, wherein the one or more processors receiving a plurality of sample signals from at least one ECG lead comprises:

receiving a first plurality of sample signals from a first ECG lead;

receiving a second plurality of sample signals from a second ECG lead; and further comprises:

cross-checking a detected first pace pulse signal from the first plurality of sample signals and a detected second pace pulse signal from the second plurality of sample signals by comparing at least one of time-stamp, peak direction, width and area between the first pace pulse signal and the second pace pulse signal.

12. The apparatus of claim 6, wherein the apparatus includes a physiological monitoring device.

* * * * *